(12) United States Patent
Hong et al.

(10) Patent No.: US 8,696,691 B2
(45) Date of Patent: Apr. 15, 2014

(54) BEAD FOR STITCHING, VACUUM CAP FOR SUCTION INTERNAL ORGAN AND APPARATUS FOR STITCHING INTERNAL ORGAN USING THE SAME

(75) Inventors: Dae Hie Hong, Gyeonggi-do (KR); Kyungmo Jung, Gyeonggi-do (KR); Kihyun Bae, Gyeonggi-do (KR); Kyeong Won Oh, Seoul (KR); Hoon Jai Chun, Seoul (KR); Yong-Sik Kim, Seoul (KR); Bora Keum, Seoul (KR)

(73) Assignee: Industrial & Academic, Collaboration Foundation, Seoul (KR)

( * ) Notice: Subject to any disclaimer, the term of this patent is extended or adjusted under 35 U.S.C. 154(b) by 1033 days.

(21) Appl. No.: 12/541,991

(22) Filed: Aug. 17, 2009

(65) Prior Publication Data

US 2010/0324574 A9    Dec. 23, 2010

Related U.S. Application Data

(63) Continuation of application No. PCT/KR2007/002809, filed on Jun. 11, 2007.

(30) Foreign Application Priority Data

Feb. 23, 2007   (KR) .................. 10-2007-0018632

(51) Int. Cl.
*A61B 17/04* (2006.01)
*A61B 17/00* (2006.01)

(52) U.S. Cl.
USPC ........................ 606/148; 600/104; 600/127

(58) Field of Classification Search
USPC .......... 606/232, 148, 144, 139, 213; 600/104, 600/127
See application file for complete search history.

(56) References Cited

U.S. PATENT DOCUMENTS

| 5,403,348 A | 4/1995 | Bonutti |
| 6,056,760 A | 5/2000 | Koike et al. |

(Continued)

FOREIGN PATENT DOCUMENTS

| EP | 0464480 A1 | 1/1992 |
| EP | 2116191 A1 | 11/2009 |

(Continued)

OTHER PUBLICATIONS

International Search Report, Nov. 23, 2007.

(Continued)

*Primary Examiner* — Julian W Woo
*Assistant Examiner* — Shaun L David
(74) *Attorney, Agent, or Firm* — Merchant & Gould

(57) ABSTRACT

A bead for stitching, a vacuum cap for suction-holding an internal organ, and an apparatus for stitching an internal organ using the vacuum cap are disclosed. The bead includes a through hole which is formed vertically through the bead so that a stitching fiber passes through the bead. At least one of both ends of the bead is inclined relative to a transverse direction of the bead. The bead is shaped to pass through a hole formed in a stitching needle. That apparatus includes an endoscope tube having a stitching needle which is movable in a longitudinal direction thereof and a suction tube for drawing air, and a vacuum cap having at an end thereof a fastening hole to which the endoscope tube is fastened. A suction hole is formed in the vacuum cap in a direction crossing the fastening hole.

11 Claims, 10 Drawing Sheets

(56) References Cited

U.S. PATENT DOCUMENTS

| | | | |
|---|---|---|---|
| 6,530,934 B1 * | 3/2003 | Jacobsen et al. | 606/157 |
| 6,719,763 B2 * | 4/2004 | Chung et al. | 606/144 |
| 2003/0208209 A1 * | 11/2003 | Gambale et al. | 606/144 |
| 2003/0236535 A1 * | 12/2003 | Onuki et al. | 606/144 |
| 2005/0096696 A1 | 5/2005 | Forsberg | |
| 2005/0251153 A1 | 11/2005 | Sakamoto et al. | |

FOREIGN PATENT DOCUMENTS

| | | |
|---|---|---|
| JP | 2004-000601 | 1/2004 |
| JP | 2005-296644 | 10/2005 |
| WO | 9807374 A1 | 2/1998 |
| WO | 0139671 A1 | 6/2001 |
| WO | WO2005069056 | 8/2008 |

OTHER PUBLICATIONS

European Search Report from corresponding EP Application No. EP 07793149.1, dated Apr. 22, 2013.

Japanese Office Action dated Aug. 27, 2013 (2 pages).

* cited by examiner

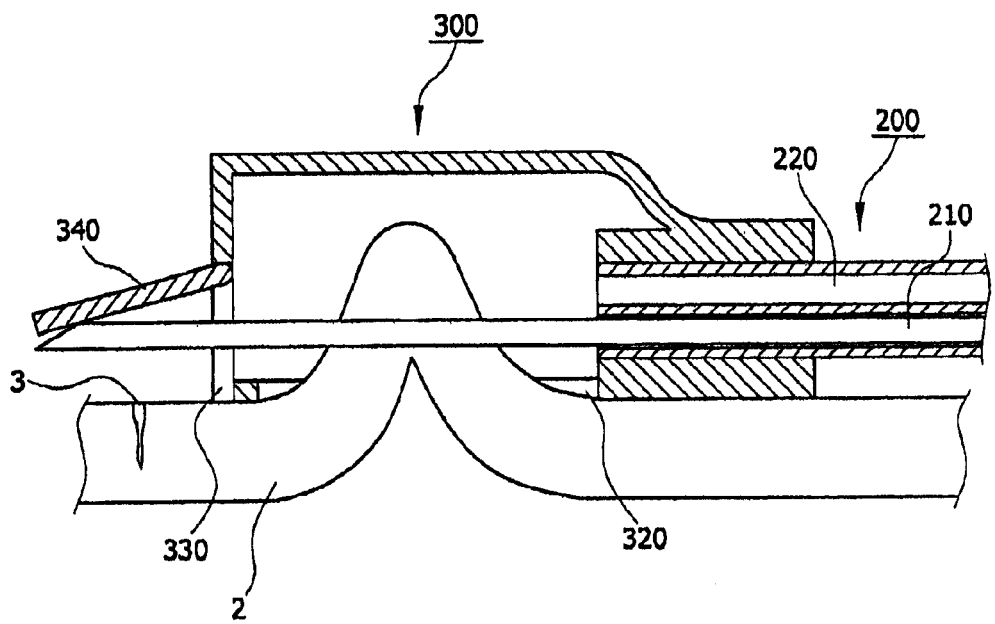
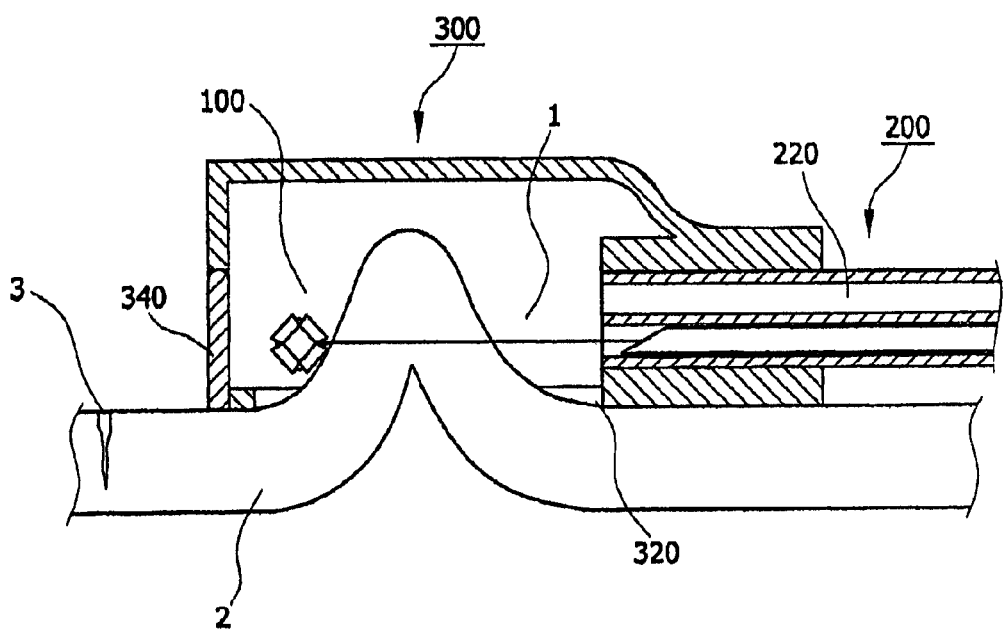

BEAD FOR STITCHING, VACUUM CAP FOR SUCTION INTERNAL ORGAN AND APPARATUS FOR STITCHING INTERNAL ORGAN USING THE SAME

This application is a continuation of International Application No. PCT/KR2007/002809, filed Jun. 11, 2007, which claims benefit of South Korean Application No. 10-2007-0018632, filed Feb. 23, 2007.

TECHNICAL FIELD

The present invention relates, in general, to a bead for stitching, a vacuum cap for suction-holding an internal organ, and an apparatus for stitching an internal organ using the vacuum cap and, more particularly, to a stitching bead which is constructed so that it is not removed from an internal organ along a stitching fiber during stitching, a vacuum cap for suction-holding an internal organ, which is constructed to prevent other internal organs or blood vessels from being injured during an operation on the internal organ, and an apparatus for stitching an internal organ using the vacuum cap.

BACKGROUND ART

Generally, an endoscope is an instrument that is inserted into an internal organ, a lesion of which cannot be examined directly unless an operation or biopsy is performed, to thus examine the internal organ. There are various types of endoscopes, including a type which is called a direct scope and comprises one tube, thus allowing a user to observe internal organs using his or her naked eyes, a type using a lens system, a type in which a camera is inserted directly into internal organs, and a fiberscope using glass fiber.

Further, recently, there have been proposed several kinds of operating instruments, which are constructed so that an instrument for stitching is attached to the endoscope and then is inserted into a patient's internal organ, thus performing an operation on the internal organ without incising the patient's body. For example, Korean Patent No. 10-0551740, which is entitled "Bead for stitching and apparatus for stitching internal organ using the same," was filed by the same applicant as the present invention, and was registered.

A conventional bead for stitching and a conventional apparatus for stitching an internal organ using the bead will be described below in detail with reference to the accompanying drawings.

FIGS. 1 to 4 are views sequentially showing the process of stitching an internal organ using the conventional stitching bead and stitching apparatus using the bead.

In the case of stitching the internal organ by the conventional stitching bead and stitching apparatus using the stitching bead, as shown in FIG. 1, a stitching needle 10 passes through an organ tissue 2 having a wound 3 which must be stitched. Next, a push pin 12 is pushed downwards so that one stitching bead 20 is discharged to the lower portion of the organ tissue 2.

When one stitching bead 20 is discharged to the lower portion of the organ tissue 2, as shown in FIG. 2, the discharged stitching bead 20 remains on the lower portion of the organ tissue 2, and only the stitching needle 10 is moved upwards. Thereafter, as shown in FIG. 3, the stitching needle moves over the wound 3 and then passes through the organ tissue 2 again. Here, the stitching bead 20 is inserted in a vertical direction. However, when the stitching needle 10 is taken out from the organ tissue, a stitching fiber 1 is pulled out through a bead hole 22. Thus, the stitching bead 20 is rotated at right angles to be in close contact with the lower surface of the organ tissue 2, as shown in FIG. 3.

A user repeats the operation of discharging the bead 2 and the operation of moving the stitching needle 10 upwards, in the state of FIG. 3. Thereby, as shown in FIG. 4, the stitching beads 20 are placed on the lower surface of the organ tissue 2 in such a way as to be positioned on opposite sides of the wound 3. In this way, the wound 3 can be stitched.

However, even though the internal organ is stitched using the conventional bead for stitching, the bead 20 may move upwards from the organ tissue 2 and the suture of the wound 3 may undesirably come unstitched, if the bead is arranged such that the longitudinal direction of the bead 20 the same as the passing direction of the stitching fiber 1. Further, whenever one stitch is made, one bead 20 must be precisely discharged. As such, the conventional bead for stitching has a drawback in that it is difficult to discharge the beads 20 precisely one by one. Further, since the conventional bead 20 has a complex structure, it is difficult to miniaturize the bead. Thus, the number of beads that may be inserted into one stitching needle 10 is limited. Hence, if many regions must be stitched, an endoscope tube 30 must be pulled out from a patient's body and be reloaded with beads 20. Afterwards, the endoscope tube 30 must be inserted into the patient's body again. As such, the conventional bead for stitching is problematic in that medical treatment is complex.

Further, the conventional apparatus for stitching the internal organ is problematic in that, while the stitching needle 10 passes through the organ tissue 2, the stitching needle 10 may injure other internal organs or blood vessels positioned under the organ tissue 2.

In order to solve the problems, a vacuum apparatus for stitching an internal organ has been proposed, which is constructed to pull up a region which must be stitched using vacuum pressure and to stitch the wound of the organ tissue.

FIG. 5 is a sectional view showing the use of the conventional vacuum apparatus for stitching the internal organ.

As shown in FIG. 5, the conventional vacuum apparatus for stitching the internal organ includes an endoscope tube 30, which is inserted into a patient's body, a stitching needle 10, which is mounted to the endoscope tube 30 in such a way as to protrude out from the endoscope tube 30, and a vacuum cap 40, which is coupled to an end of the endoscope tube 30. Further, the endoscope tube 30 is provided with a suction tube (not shown), which draws air from the interior of the vacuum cap 40.

Thus, after an operator puts the vacuum cap 40 on an organ tissue 2 around a region having the wound 3, air is drawn from the vacuum cap 40 using the suction tube, so that vacuum pressure is created in the vacuum cap 40. As such, when the vacuum pressure is created in the vacuum cap 40, the organ tissue 2 of a region corresponding to the interior of the vacuum cap 40 is pulled towards the endoscope tube 30. Thus, even though the vacuum needle 10 passes through the organ tissue 2, the possibility of injuring other internal organs or blood vessels positioned under the organ tissue 2 is reduced.

In order to perform the normal discharge of the beads, the stitching needle 10 must be inserted sufficiently deeply into the organ tissue. However, since it is difficult to precisely know the depth to which the stitching needle 10 is inserted, the stitching needle 10 is frequently inserted into the organ tissue too deeply. Therefore, the conventional vacuum apparatus' for stitching the internal organ is problematic in that it cannot completely prevent other internal organs or blood vessels from being injured by the stitching needle 10.

DISCLOSURE

Technical Problem

Accordingly, the present invention has been made keeping in mind the above problems occurring in the prior art, and an object of the present invention is to provide a bead for stitching, which is constructed so that, after it passes through an organ tissue and is discharged out of the organ tissue, the bead does not come back to the interior of the organ tissue, and which has a simple structure, thus permitting miniaturization of the bead.

Another object of the present invention is to provide a vacuum cap for suction-holding an internal organ and an apparatus for stitching the internal organ using the vacuum cap, which are constructed to prevent other internal organs or blood vessels from being injured, even though a stitching needle is inserted deeply enough to pass completely through a region on which an operation is being performed.

Technical Solution

In order to accomplish the above objects, the present invention provides a bead for stitching, including a through hole which is formed vertically through the bead so that a stitching fiber passes through the bead, at least one of both ends of the bead being inclined relative to a transverse direction of the bead, the bead being shaped to pass through a hole formed in a stitching needle.

The both ends of the bead are formed to be symmetrical with respect to a transverse central axis.

According to the present invention, a vacuum cap for suction-holding an internal organ is coupled to an end of an endoscope tube having a suction tube and suction-holds part of the internal organ.

A suction hole is formed in a direction crossing a direction in which the endoscope tube is coupled with the vacuum cap.

The suction hole is formed to be at right angles with a line extending in the direction in which the endoscope tube is coupled with the vacuum cap.

An outlet hole is formed in an end of the vacuum cap, which is opposite an end coupled to the endoscope tube, and the vacuum cap further includes a door for opening or closing the outlet hole.

The door closes the outlet hole, and is pushed outwards by external force, thus opening the outlet hole. The door is restored and closes the outlet hole when external force is eliminated.

The door is hinged at an end thereof to an edge of the outlet hole, and further comprises an elastic means for applying elastic force to the door in a direction in which the outlet hole closes.

The door is made of an elastic material, and is secured at an end thereof to an edge of the outlet hole.

According to the present invention, an apparatus for stitching an internal organ includes an endoscope tube having a stitching needle which is movable in a longitudinal direction thereof, and a suction tube for drawing air; and a vacuum cap having at an end thereof a fastening hole to which the endoscope tube is fastened. A suction hole is formed in the vacuum cap in a direction crossing the fastening hole.

The suction hole is formed to be at right angles with a line extending along a direction in which the endoscope tube is coupled with the vacuum cap.

An outlet hole is formed to be opposite the fastening hole so that a tip of the stitching needle is ejected out through the outlet hole. The apparatus further includes a door for opening or closing the outlet hole.

The door closes the outlet hole, and is pushed outwards by the ejected stitching needle, thus opening the outlet hole. The door is restored and closes the outlet hole when the stitching needle is retracted into the endoscope tube.

The door is hinged at an end thereof to an edge of the outlet hole, and further includes an elastic means for applying elastic force to the door in a direction in which the outlet hole closes.

The door is made of an elastic material, and is secured at an end thereof to an edge of the outlet hole.

Advantageous Effects

According to the present invention, a bead for stitching is advantageous in that it is constructed so that, after it passes through an organ tissue and is discharged out of the organ tissue, the bead does not come back to the interior of the organ tissue, thus preventing a stitched region from undesirably coming unstitched, and it is very simple in structure, thus permitting miniaturization, therefore increasing the number of stitches that can be made for a single insertion of an endoscope tube.

Further, a vacuum cap for suction-holding an internal organ and an apparatus for stitching the internal organ using the vacuum cap are advantageous in that, even though a product is miniaturized, a stitching needle can be inserted sufficiently deeply, and other internal organs or blood vessels are not injured by the insertion of the stitching needle.

DESCRIPTION OF DRAWINGS

FIGS. 10 to 14 are views showing the use of the apparatus for stitching the internal organ, according to the present invention.

MODE FOR INVENTION

Hereinafter, a bead for stitching, a vacuum cap for suction-holding an internal organ, and an apparatus for stitching an internal organ, according to the preferred embodiment of the present invention, will be described in detail with reference to the accompanying drawings.

Figure 6:
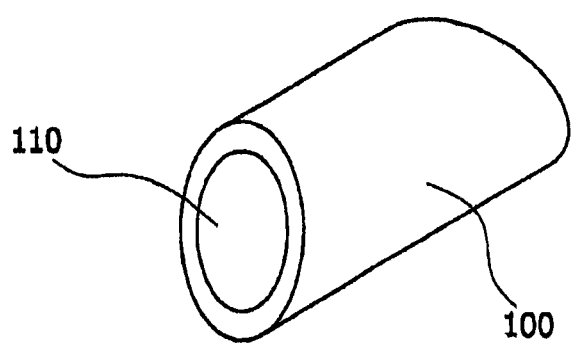
FIG. 6 is a perspective view showing a bead for stitching, according to the present invention.

FIG. 6 is a perspective view showing a bead 100 for stitching, according to the present invention.

As shown in FIG. 6, the stitching bead 100 according to the present invention has a through hole 110 therein so that a stitching fiber 1 passes through the stitching bead. The through hole 110 is formed vertically through the stitching bead 100. Both ends of the stitching bead 100 are formed obliquely relative to the transverse direction of the bead. As such, when both ends of the stitching bead 100 are formed obliquely, one vertical edge of the stitching bead is short, and the other vertical edge is long. Here, it is preferable that both ends of the stitching bead be symmetrical with respect to a transverse central axis.

According to this embodiment, both ends of the stitching bead 100 are formed obliquely. However, it is possible for only one of the ends to be formed obliquely.

Figure 7:
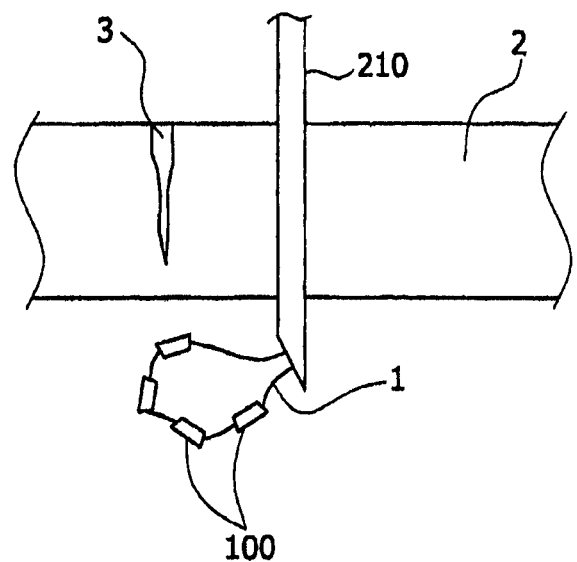
FIGS. 7 and 8 are views showing the use of the stitching bead, according to the present invention.
Figure 8:
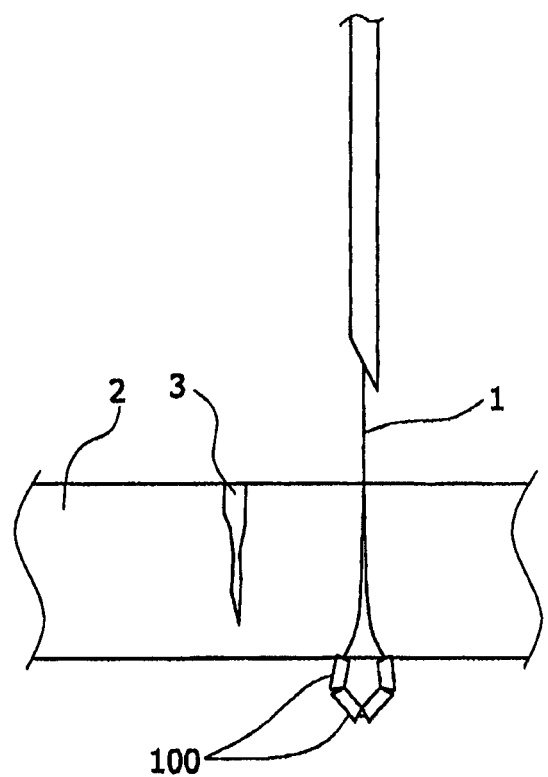

FIGS. 7 and 8 are views showing the use of the stitching bead 100, according to the present invention.

According to the present invention, the stitching beads 100 are connected to each other in a row by the stitching fiber 1 and are positioned in the stitching needle 210. In such a state, as shown in FIG. 7, when the stitching needle 210 passes through the organ tissue 2, a plurality of (preferably, three or more) stitching beads 100 is discharged out of the organ tissue 2 by an operator's manipulation. At this time, the stitching fiber 1, passing through the stitching beads 100, has a loop shape.

After the stitching beads 100 have been discharged, the operator moves the stitching needle 210 upwards so that it returns to its original position. At this time, the stitching fiber 1 is pulled upwards along the stitching needle 210. Thereby, the stitching beads 100, connected by the stitching fiber 1, come into close contact with each other. In order to minimize the length of the arranged stitching beads as the stitching fiber 1 is pulled, as shown in FIG. 8, the stitching beads 100 are arranged such that the shorter edge of each stitching bead is placed inside and the longer edge thereof is placed outside, thus forming a loop shape. In such a state, the stitching beads 100 are secured to the lower surface of the organ tissue 2.

As such, when the plurality of stitching beads 100 is arranged in the loop shape, the stitching beads 100 do not pass through the organ tissue 2 to be removed from the organ tissue 2, even if the stitching fiber 1 is pulled with strong force. Therefore, the stitching bead of the invention is advantageous in that undesirable unstitching is prevented.

Further, the stitching bead 100 of the invention is advantageous in that its structure is simple, so that it is easy to manufacture and its manufacturing cost is low, in comparison with the conventional stitching bead 20 of FIGS. 1 to 4. Furthermore, the stitching bead 100 of this invention has a simpler structure than the conventional stitching bead 20, so that the miniaturization of the stitching bead is possible. As such, if the size of the stitching bead 100 is reduced, a plurality of stitching beads may be inserted into one stitching needle 210. Thus, the present invention is advantageous in that the number of stitches that can be performed is considerably increased with a single operation.

Figure 9:
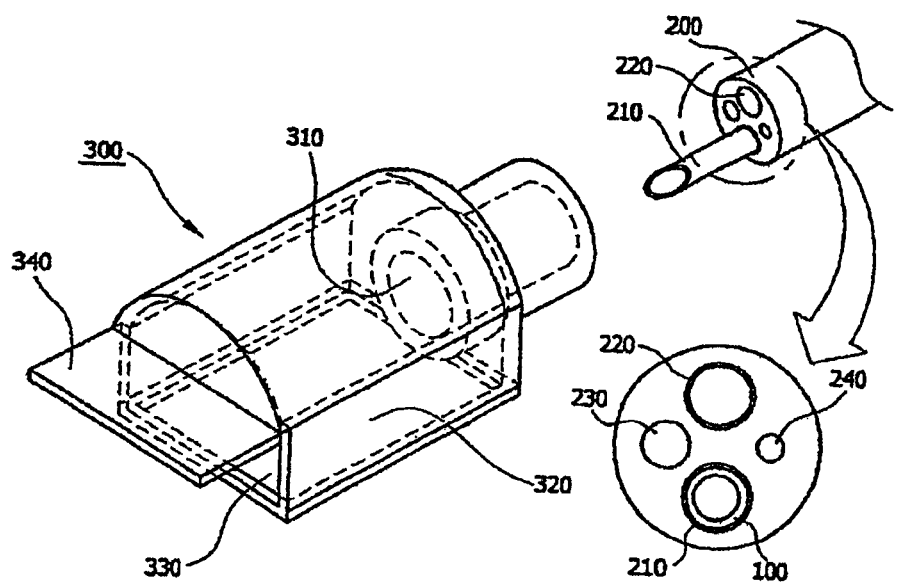
FIG. 9 is an exploded perspective view showing an apparatus for stitching an internal organ, according to the present invention.

FIG. 9 is an exploded perspective view showing an apparatus for stitching an internal organ, according to the present invention.

As shown in FIG. 9, the stitching apparatus according to the present invention includes an endoscope tube 200 which is inserted into a patient's body and is used to stitch the internal organ, and a vacuum cap 300 which is coupled to an end of the endoscope tube 200 and suction-holds a region on which an operation is to be performed.

The endoscope tube 200 is provided with a stitching needle 210, a suction tube 220, a camera 230, and an illumination means 240. The stitching needle is constructed to move in a longitudinal direction thereof in response to an operator's manipulation. The suction tube draws air from the vacuum cap 300 such that vacuum pressure is generated in the vacuum cap 300. The operator observes the region on which the operation is to be performed through the camera. The illumination means radiates light onto the region which is to be operated on. A plurality of stitching beads 100, connected via a stitching fiber 1, is arranged in a row in the stitching needle 210.

Further, the beads arranged in the stitching needle 210 may be discharged out of the stitching needle 210 by an operator's manipulation. The construction in which the stitching needle 210 moves in the longitudinal direction thereof to be extended out of or retracted into the endoscope tube 200, and the construction in which the stitching beads 100 are discharged out of the stitching needle 210, are variously embodied in the conventional apparatus for stitching the internal organ. Hence, the detailed description of the construction will be omitted therein.

The vacuum cap 300 is a part for suction-holding an organ tissue 2 of a region which must be operated on, thus preventing other internal organs or blood vessels from being injured when the stitching needle 210 passes through the organ tissue 2. A fastening hole 310 is formed in one end of the vacuum cap so that the endoscope tube can be fastened to the fastening hole. A suction hole is formed in the lower surface of the vacuum cap so that a region that must be operated on can be held by suction.

According to this embodiment, the endoscope tube 200 is directly fastened to the fastening hole 310, which is formed in the vacuum cap 300. However, the vacuum cap 300 and the endoscope tube 200 may be coupled to each other via an additional coupling tube. Further, a sealing member may be provided so as to prevent air from leaking out through the junction of the vacuum cap 300 and the endoscope tube 200.

Figure 1:
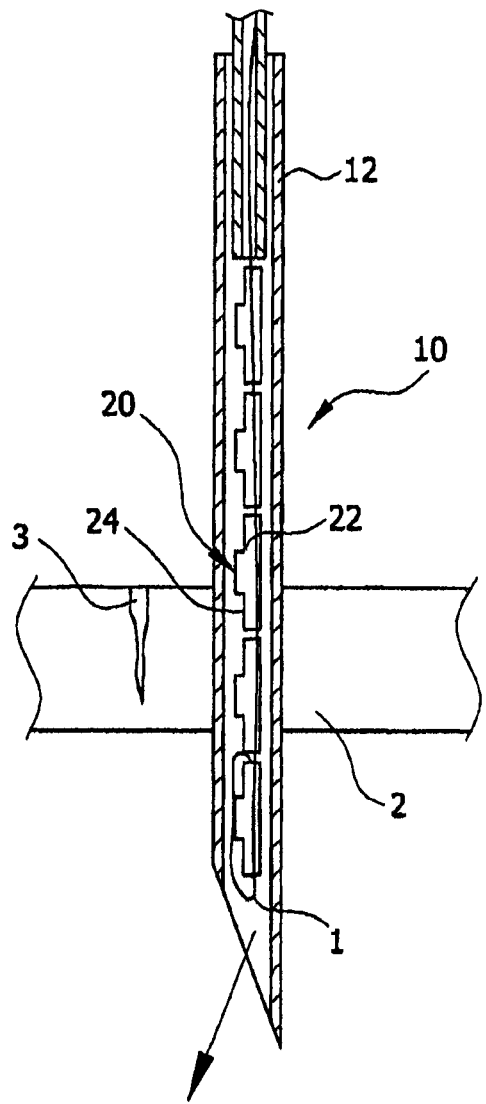
FIGS. 1 to 4 are views sequentially showing the process of stitching an internal organ using a conventional stitching bead and a conventional apparatus for stitching the internal organ using the stitching bead.
Figure 2:
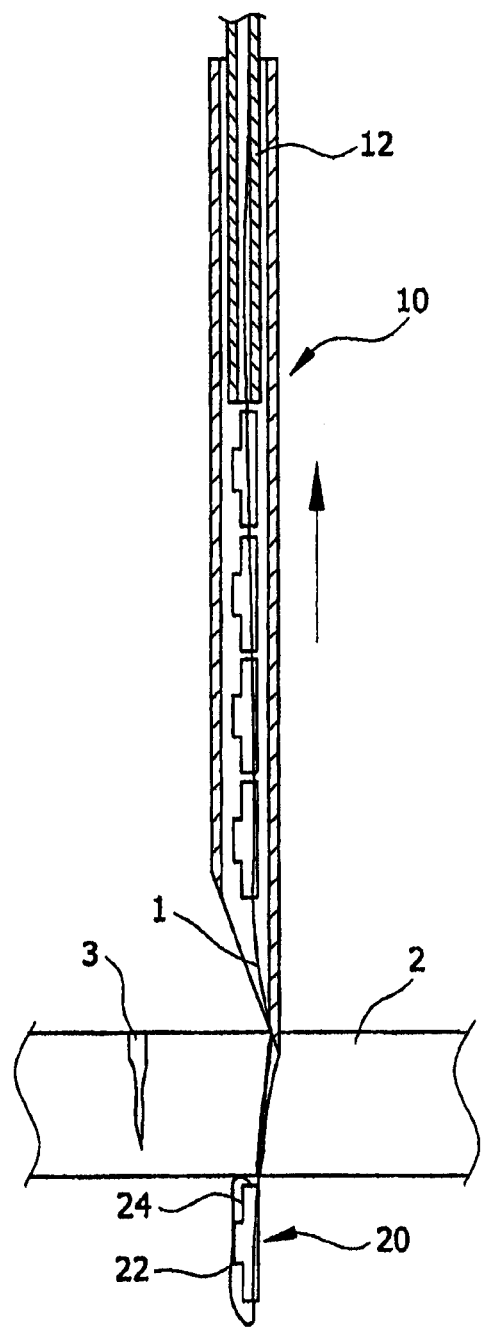
Figure 3:
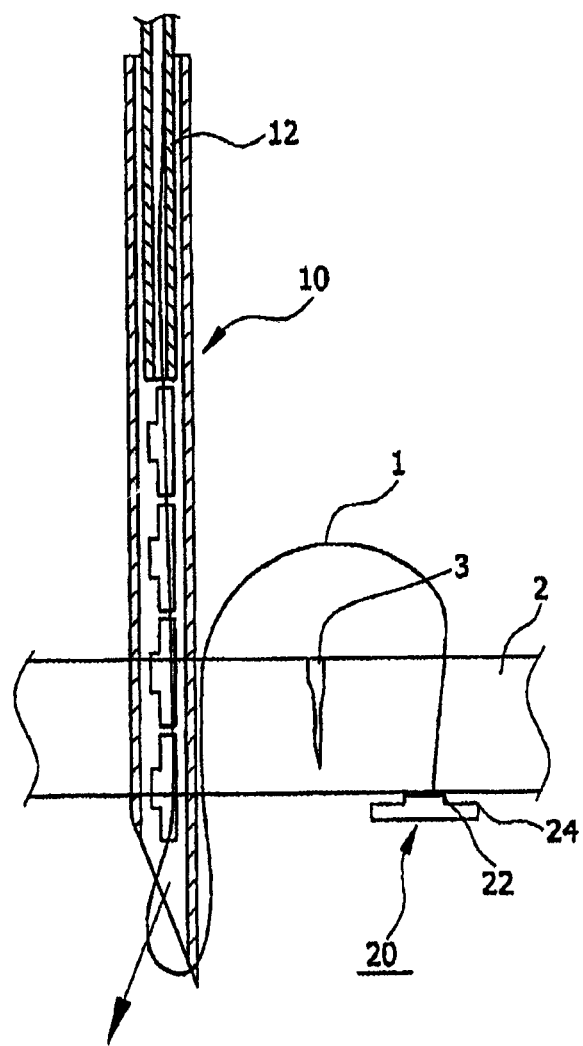
Figure 4:
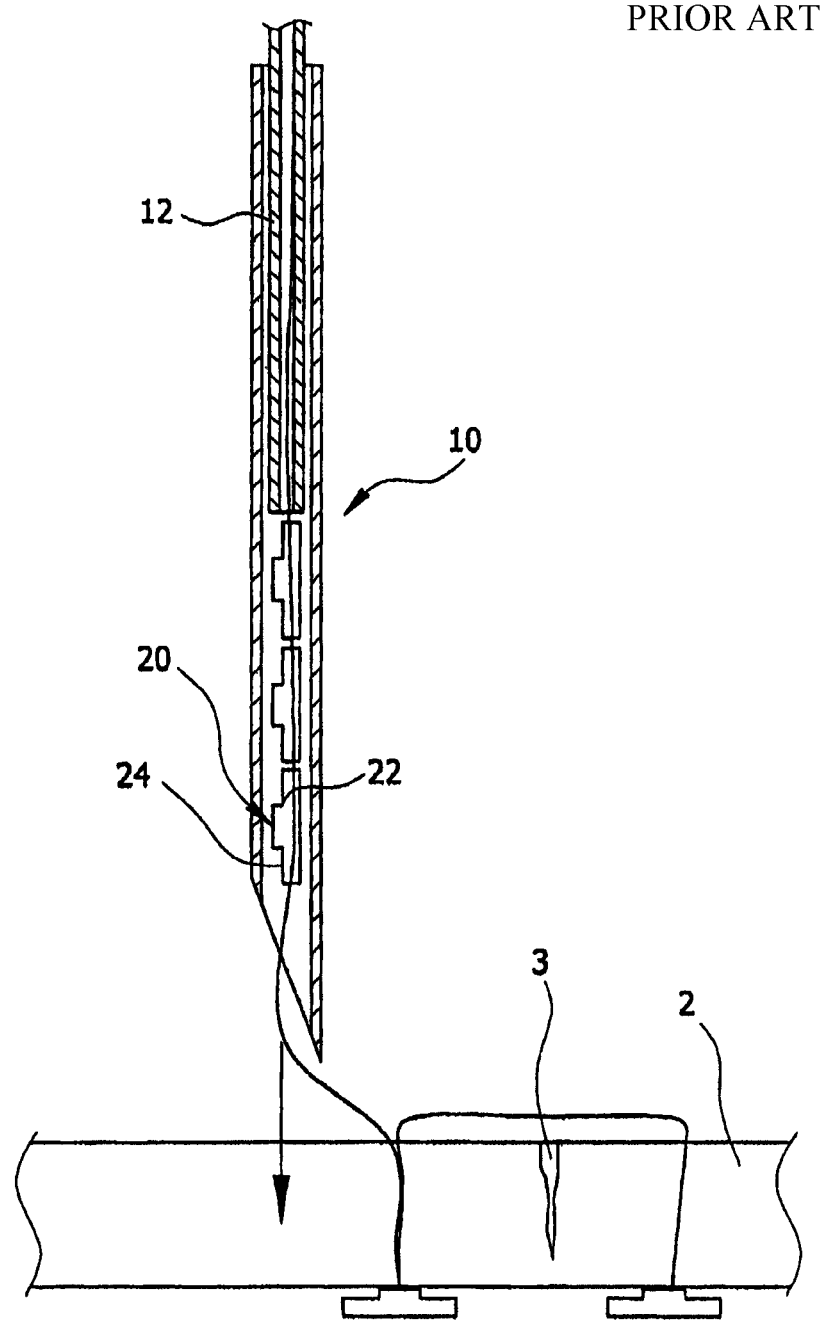
Figure 5:
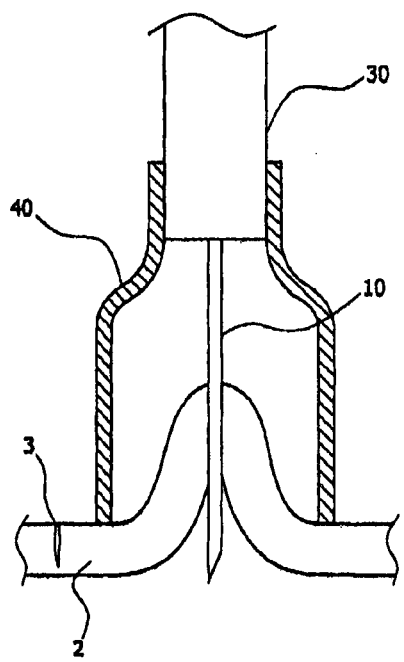
FIG. 5 is a sectional view showing the use of a conventional vacuum apparatus for stitching an internal organ.

The conventional vacuum cap 40, shown in FIG. 5 is problematic in that the endoscope tube 30 is mounted to the upper portion of the vacuum cap, so that the tip of the stitching needle 10 passes through the organ tissue 2 when the stitching needle 10 is ejected out, and thereby other internal organs or blood vessels positioned under the organ tissue 2 may be injured. However, the vacuum cap 300 of the present invention is constructed so that the endoscope tube 200 is mounted to one side of the vacuum cap. Thus, even if the stitching needle 210 is ejected out, other internal organs or blood vessels positioned under the organ tissue 2 are not injured.

In a detailed description, the suction hole 320 of the vacuum cap 300 is not formed along an extrapolated line in the direction in which the vacuum cap is coupled with the endoscope tube 200, but is formed in a direction crossing the direction in which the vacuum cap is coupled with the endoscope tube 200. Thus, the stitching needle 210, ejected out from the endoscope tube 200, cannot pass through the suction hole 320 to thus injure other internal organs or blood vessels which are positioned outside the organ tissue 2. In order to most efficiently prevent the stitching needle 210 from entering the suction hole 320, it is preferable that the suction hole 320 be at right angles with a line extending in the direction in which the vacuum cap is coupled with the endoscope tube 200.

Further, an outlet hole 330 is formed opposite the fastening hole 310, to which the endoscope tube 200 is fastened, so that the tip of the stitching needle 210 passes through the outlet hole. A door 340 is provided to open or close the outlet hole 330.

The door 340 functions to close and seal the outlet hole 330, thus preventing the external air from flowing into the vacuum cap when vacuum pressure is generated in the vacuum cap 300. Further, when the door 340 is pushed outwards by external force, the door is rotated to open the outlet hole 330. Meanwhile, when the external force is eliminated, the door is restored to its original position, thus closing the outlet hole 330.

The function and detailed construction of the door 340 will be described below with reference to the accompanying drawings.

FIGS. 10 to 14 are views showing the use of the apparatus for stitching the internal organ, according to the present invention.

Figure 10:
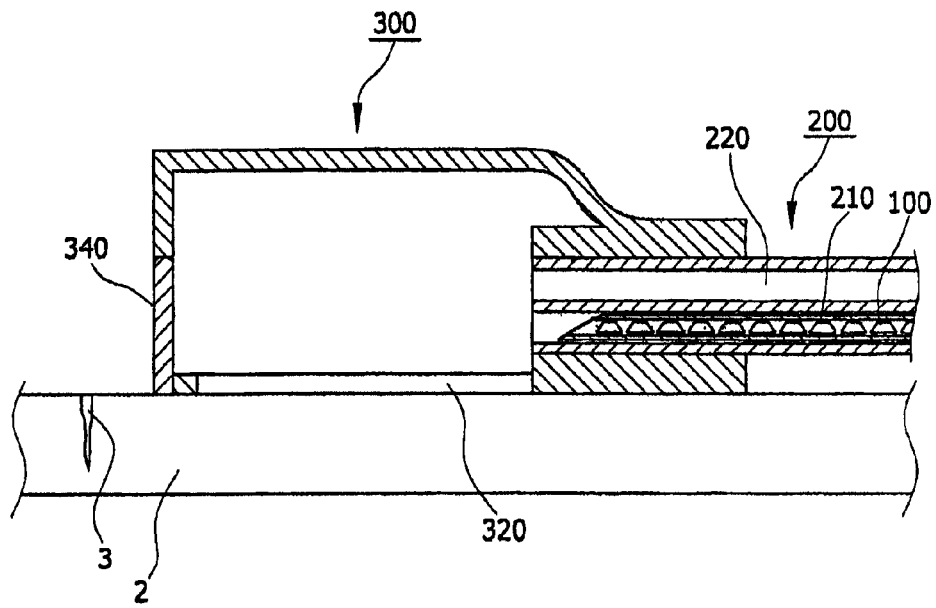

As shown in FIG. 5, the conventional apparatus for stitching the internal organ is constructed so that it is seated on the organ tissue 2 in a vertical direction. Unlike the conventional stitching apparatus, the apparatus for stitching the internal organ according to the present invention is seated on the organ tissue 2 in such a way as to be parallel to the organ tissue, as shown in FIG. 10. An operator places the vacuum cap 300 such that the suction hole 320 covers the region having the wound 3, that is, a region which is to be operated on. Thereafter, air is drawn from the vacuum cap 300 through the suction tube 220 (see FIG. 9) which is provided in the endoscope tube 200.

Figure 11:
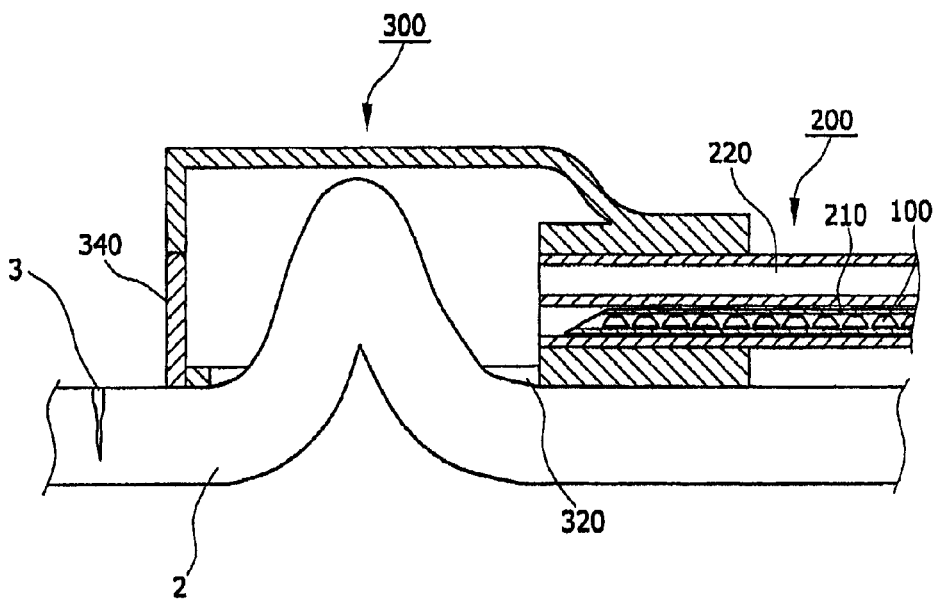

When air is exhausted from the vacuum cap 300, vacuum pressure is generated in the vacuum cap 300. Thus, as shown in FIG. 11, part of the organ tissue 2 corresponding to the suction hole 320, that is, the region which is to be operated on, is drawn into the vacuum cap 300.

As such, when the region which is to be operated on is drawn into the vacuum cap 300, the stitching needle 210 is ejected out by an operator's manipulation and passes through the region which must be operated on. Since the stitching needle 210 passes only through the region that is drawn into the vacuum cap 300, other internal organs or blood vessels, positioned outside the organ tissue 2, are not injured.

In order to more reliably pass the stitching needle 210 through the region on which the operation is to be performed, the distance that the stitching needle 210 can be ejected out without interference by the sidewall of the vacuum cap 300 must be long. As such, in order to increase the distance that the stitching needle 210 is ejected, the vacuum cap 300 must be manufactured to be long in the longitudinal direction of the stitching needle 210. However, when the vacuum cap 300 is manufactured to be long, it is difficult to insert the vacuum cap 300 into a patient's body, and in addition, the patient feels uncomfortable.

In order to solve the problem, the vacuum cap 300 of this invention has an outlet hole 330 which is formed in the line along which the stitching needle 210 is ejected, that is, in a sidewall of the vacuum cap, which faces the fastening hole 310, so that the tip of the stitching needle 210 passes through the outlet hole 330. Thereby, the outlet hole allows the stitching needle 210 to be ejected farther, obviating the necessity to increase the length of the vacuum cap 300.

In this case, if the outlet hole 330 is always kept open, external air is fed through the outlet hole 330 into the vacuum cap, even though air is drawn from the vacuum cap 300 using the suction tube 220. Thus, no vacuum pressure is generated in the vacuum cap 300. In order to avoid this, the vacuum cap 300 of this invention is provided with the door 340 which opens or closes the outlet hole 330. When the suction tube 220 draws air from the vacuum cap 300, the door 340 closes the outlet hole 330, thus preventing external air from flowing into the vacuum cap 300. Meanwhile, when the stitching needle 210 is ejected out, the door is pushed and thus opened by the stitching needle 210.

As such, when the outlet hole 330 and the door 340 are provided on the sidewall of the vacuum cap 300, the stitching needle 210 is positioned outside the vacuum cap 300 after the tip of the stitching needle passes through part of the organ tissue 2. That is, the stitching needle 210 can be ejected farther than the length of vacuum cap 300. Thus, the present invention is advantageous in that miniaturization of the vacuum cap 300 is possible.

The door 340 is constructed so that it is restored and closes the outlet hole 330 when the stitching needle 210 returns to the interior of the endoscope tube 200. That is, one end (the upper end in this embodiment) of the door 340 is hinged to an edge (the upper edge in this embodiment) of the outlet hole 330. The door is provided with an elastic means (hot shown) which applies elastic force to the door 340 in the direction in which the outlet hole 330 is closed. Alternatively, the door 340 may be made of an elastic material. In this case, the door is coupled to an edge of the outlet hole 330 in such a way as to elastically close the outlet hole 330, as long as external force is not applied to the door.

When the stitching needle 210 is ejected in the state of FIG. 11, as shown in FIG. 12, the tip of the stitching needle 210 passes through the region that is to be operated on, and thereafter pushes the door 340, so that the tip is positioned outside the vacuum cap 300. Although the door 340 is opened as shown in FIG. 12, by which vacuum pressure is released from the vacuum cap 300, the part of the organ tissue 2 that is drawn into the vacuum cap 300 is penetrated by the stitching needle 210. Thus, that part of the organ tissue is held in the vacuum cap 300. In the state of FIG. 12, the plurality of stitching beads 100 provided in the stitching needle 210 is discharged out of the stitching needle 210. Afterwards, the stitching needle 210 is returned to the interior of the endoscope tube 200.

As such, when the stitching needle 210 has returned to the interior of the endoscope tube, as shown in FIG. 13, the door 340 is restored, thus closing the outlet hole 330, and the plurality of stitching beads 100 is held outside the region which is to be operated on.

Figure 14:
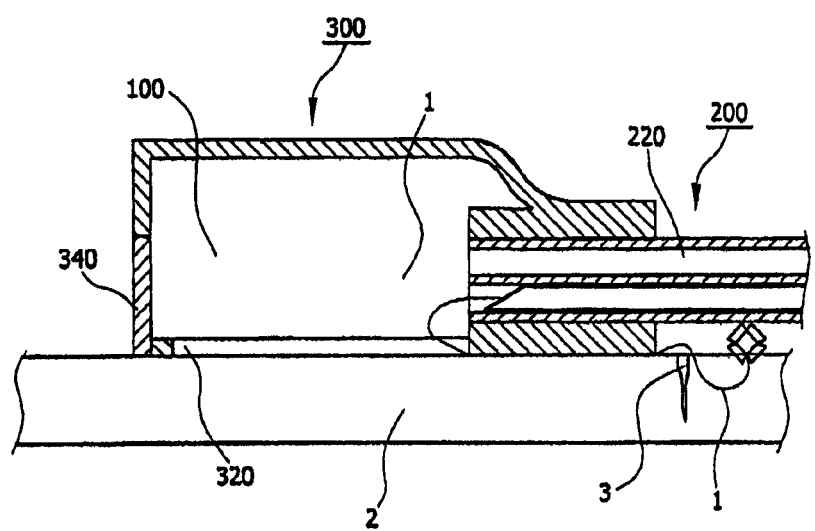

When the stitching beads 100 are held as shown in FIG. 13, an operator moves the vacuum cap 300 such that the suction hole 320 is located at a position after having moved over the wound 3, as shown in FIG. 14. In this state, the process of suction-holding and stitching the organ tissue 2 is repeated, so that the wound 3 is sutured. Since the process of suction-holding and stitching the organ tissue 2 is the same as the process shown in FIGS. 11 to 13, the detailed description of the process will be omitted herein.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. A vacuum cap (300) for suction-holding an internal organ, the vacuum cap being configured to be coupled to an end of an endoscope tube (200) having a suction tube (220) and being configured to suction-hold part of the internal organ, the vacuum cap comprising:

a top portion, a side portion, and a bottom portion;
a suction hole (320) formed in the bottom portion only in a direction crossing a direction in which the endoscope tube (200) is coupled with the vacuum cap, wherein an outlet hole (330) is formed in an end of the vacuum cap, which is opposite an end coupled to the endoscope tube (200), and the vacuum cap further comprises a door (340) for opening or closing the outlet hole (330), a lower edge of the door configured to pivot relative to the top portion.

2. The vacuum cap (300) according to claim 1, wherein the suction hole (320) is formed to be at right angles with a line extending in the direction in which the endoscope tube (200) is coupled with the vacuum cap.

3. The vacuum cap (300) according to claim 1, wherein the door (340) closes the outlet hole (330), and is pushed outwards by external force, thus opening the outlet hole (330), the door being restored and closing the outlet hole (330) when external force is eliminated.

4. The vacuum cap (300) according to claim 3, wherein the door (340) is hinged at an end thereof to an edge of the outlet hole (330), and further comprises elastic means for applying elastic force to the door (340) in a direction in which the outlet hole (330) closes.

5. The vacuum cap (300) according to claim 3, wherein the door (340) is made of an elastic material, and is secured at an end thereof to an edge of the outlet hole (330).

6. An apparatus for stitching an internal organ, comprising:
   an endoscope tube (200) having a stitching needle (210) which is movable in a longitudinal direction thereof, and a suction tube (220) for drawing air; and
   a vacuum cap (300) having side walls that extend downwardly to a bottom, wherein the side walls include a fastening hole (310) to which the endoscope tube (200) is fastened, a suction hole (320) being formed within the bottom of the vacuum cap in a direction crossing the fastening hole (310),
   wherein an outlet hole (330) is formed to be opposite the fastening hole (310) so that a tip of the stitching needle (210) is ejected out through the outlet hole, and the apparatus further comprises a door (340) for opening or closing the outlet hole (330).

7. The apparatus according to claim 6, wherein the suction hole (320) is formed to be at right angles with a line extending along a direction in which the endoscope tube (200) is coupled with the vacuum cap.

8. The apparatus according to claim 6, wherein the door (340) closes the outlet hole (330), and is pushed outwards by the ejected stitching needle (210), thus opening the outlet hole (330), the door being restored and closing the outlet hole (330) when the stitching needle (210) is retracted into the endoscope tube.

9. The apparatus according to claim 8, wherein the door (340) is hinged at an end thereof to an edge of the outlet hole (330), and further comprises elastic means for applying elastic force to the door (340) in a direction in which the outlet hole (330) closes.

10. The apparatus according to claim 8, wherein the door (340) is made of an elastic material, and is secured at an end thereof to an edge of the outlet hole (330).

11. The apparatus according to claim 6, wherein the endoscope tube (200) comprises:
    a camera (230) for causing an operator to observe a region on which is to be operated; and
    illumination means (240) for radiating light onto the region on which is to be operated.

* * * * *